United States Patent [19]

Wemple et al.

[11] Patent Number: 4,772,706

[45] Date of Patent: Sep. 20, 1988

[54] PROCESS FOR QUINOLINE-3-CARBOXYLIC ACID ANTIBACTERIAL AGENTS

[75] Inventors: James N. Wemple; James R. Zeller, both of Holland; John M. Domagala, Canton, all of Mich.

[73] Assignee: Warner-Lambert Company, Morris Plains, N.J.

[21] Appl. No.: 818,450

[22] Filed: Jan. 13, 1986

[51] Int. Cl.[4] .................. C07D 215/22; C07D 451/04; C07D 471/04; C07D 471/08

[52] U.S. Cl. ......................................... 544/349; 544/3; 544/53; 544/54; 544/55; 544/56; 544/58.2; 544/58.6; 544/62; 544/63; 544/96; 544/98; 544/128; 544/238; 544/333; 544/336; 544/351; 544/363; 546/15; 546/16; 546/113; 546/122; 546/126; 546/153; 546/156; 558/389; 560/51

[58] Field of Search ............... 546/156, 15, 16, 153, 546/113, 122, 126, 123; 544/363, 349, 3, 53–56, 58.2, 58.6, 62, 63, 96, 98, 128, 238, 333, 336, 351

[56] References Cited

U.S. PATENT DOCUMENTS

| | | | |
|---|---|---|---|
| 4,556,658 | 12/1985 | Grohe et al. | 544/363 |
| 4,680,401 | 7/1987 | Grohe | 546/156 |
| 4,699,992 | 10/1987 | Grohe | 544/363 |

FOREIGN PATENT DOCUMENTS 899399 7/1984 Belgium .
168737 1/1986 European Pat. Off. .

OTHER PUBLICATIONS

Jerry March, "Advanced Organic Chemistry" (2nd ed.) McGraw-Hill Publishers (1977) pp. 418–419 and 441 and 572.
Gilman and Spatz, *J. Am. Chem. Soc.*, vol. 63, p. 1553 (1941).
Nakanishi et al., Chem. Abstracts, 71:101735q (1969).
Kozello et al., Pharmaceutical Chemistry Journal (Eng. Transl. of Khimiko–Farmatsevitcheskii Zhurnal) vol. 5, (1971) pp. 21–22.

*Primary Examiner*—Donald G. Daus
*Assistant Examiner*—E. Bernhardt
*Attorney, Agent, or Firm*—Ronald A. Daignault

[57] ABSTRACT

An improved process for the preparation of 7-substituted amino-1-alkyl- or cyclopropyl-6,8-difluoro-1,4-dihydro-4-oxo-3-quinolinecarboxylic acids is described where tetrafluorobenzoyl chloride is converted in three operations via 1-alkyl or 1-cycloalkyl-1,4-dihydro-6,7,8-trifluoro-4-oxoquinoline-3-carbonitrile which in a separate step or in situ is displaced and hydrolyzed to the desired product.

20 Claims, No Drawings

PROCESS FOR QUINOLINE-3-CARBOXYLIC ACID ANTIBACTERIAL AGENTS

BACKGROUND OF THE INVENTION

Belgium Pat. No. 899,399 describes certain 7-piperazine-1-cyclopropyl-6,8-difluoro-1,4-dihydro-4-oxo-3-quinolinecarboxylic acids. German Offenlegungschrift 3318145 describes various 7-amino-1-cyclopropyl-6,8-difluoro-1,4-dihydro-4-oxo-3-quinolinecarboxylic acids. European Pat. Publication No. 106489 describes 7-cyclic amino-1-cyclopropyl-6,8-difluoro-1,4-dihydro-4-oxo-3-quinolinecarboxylic acids.

All of the above compounds are useful as antibacterial agents and have been described as being prepared by displacement of a 7-fluoro atom from a compound of the formula

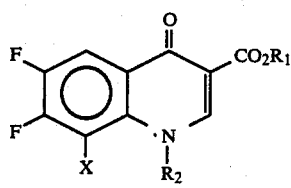

wherein X is hydrogen or fluorine; $R_1$ is hydrogen or lower alkyl, and $R_2$ is alkyl of one to three carbon atoms or cycloalkyl of three to six carbon atoms, with the appropriate amine.

The object of the present invention is an improved process for preparing the compounds described above using a 1-alkyl or cycloalkyl-6,7,8-trifluoro-1,4-dihydro-4-oxo-quinoline-3-carbonitrile for the displacement reaction with the appropriate amine and then hydrolysis of the nitrile group and any protecting group present to give the final product.

The present method provides better quality material with fewer purification procedures, step-saving by being able to carry out the reaction in fewer "pots," and high overall yields from tetrafluorobenzoyl chloride.

SUMMARY OF THE INVENTION

Accordingly a first aspect of the present invention is an improved process for the preparation of a compound of the formula

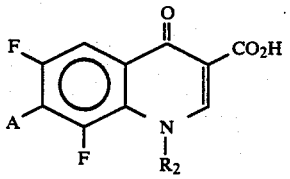

and the pharmaceutically acceptable acid addition or base salts thereof, wherein A is a substituted amino group and $R_2$ is alkyl of one to three carbon atoms or cycloalkyl of three to six carbons, which comprises:

(a) reacting tetrafluorobenzoyl chloride with tert.-butyl cyanoacetate in the presence of at least two equivalents of base to give after acid work-up a compound of the formula

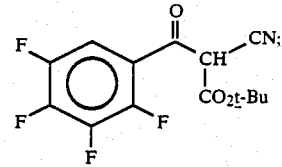

(b) treating the compound of Formula II with triethyl or trimethylorthoformate and acetic anhydride at reflux, followed by at least one equivalent of an amine of the formula $R_2NH_2$ at ambient temperature, and followed by heating at reflux in the presence of at least one equivalent of a tertiary amine and in a polar aprotic solvent to afford a compound of the formula

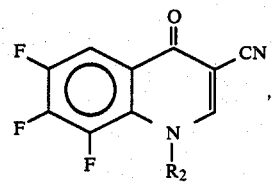

and (c) reacting a compound of Formula III with a substituted amine A followed by acid hydrolysis to provide a compound of Formula I in the form of its corresponding pharmaceutically acceptable acid addition salt, and if desired, converting by known methods said salt to the corresponding free acid or a pharmaceutically acceptable base salt thereof.

A second aspect of the present invention is a process for the preparation of a compound of the Formula I which comprises reacting a compound of the Formula III with a substituted Amine A followed by acid hydrolysis to afford a compound of Formula I in the form of its corresponding pharmaceutically acceptable acid addition salt.

A third aspect of the present invention are the novel intermediates of the Formula III which are useful in the preparation of antibacterial agents of the Formula I.

A fourth aspect of the present invention is the discovery that the ring closure reaction which occurs in the last sequence of process step (b) in the first aspect of the invention can be carried out in a general way with a variety of intermediates such as compounds of the formula

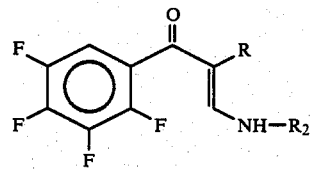

wherein R is CN or COOR' in which R' is alkyl of one to six carbon atoms or aralkyl, by heating at reflux a compound of Formula IV in the presence of at least one equivalent of a tertiary amine in a polar aprotic solvent to afford a compound of the formula

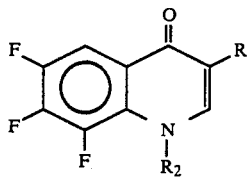

DETAILED DESCRIPTION

The term "alkyl" in the present invention refers to a one to three or one to six carbon straight or branched hydrocarbon radical as specified, such as, e.g., methyl, ethyl, 1- or 2-propyl, and the like, but preferably ethyl.

"Cycloalkyl" refers to a three to six-membered saturated hydrocarbon ring such as, e.g., cyclobutyl, cyclopentyl, cyclohexyl, and preferably cyclopropyl.

"Aralkyl" means a phenyl or substituted phenyl attached to an alkyl radical as defined above. Substituted phenyl means phenyl substituted by common aromatic substituents such as alkyl, alkoxy, halogen, hydroxy, nitro, or trifluoromethyl. The preferred aralkyl radical is benzyl.

By substituted amino group, there is included a mono- or dialkylamino group of one to four carbon atoms, straight or branched, which alkyl portion may be optionally substituted by hydroxy, amino, methylamino or dimethylamino; a five- to six-membered heterocyclic amino group, which ring may be interrupted by another heteroatom such as oxygen, sulfur, —SO—, —SO$_2$ or N—R$_3$, and which ring may be substituted by alkyl of one to three carbon atoms, hydroxy, alkoxy of one to three carbon atoms, amino, methylamino, ethylamino, aminomethyl, aminoethyl, alkylaminoethyl, or alkylaminomethyl, in which alkyl is one to three carbon atoms, and wherein R$_3$ is hydrogen, alkyl of one to four carbon atoms or cycloalkyl having three to six carbon atoms.

Also included as substituted amino is a group of the formula

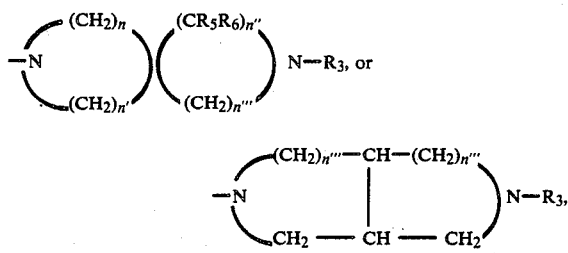

wherein
R$_3$ is as defined above, and
n is 1, 2, 3, or 4;
n' is 1, 2, 3, or 4 wherein n+n' is a total of 2, 3, 4, or 5;
n'' is 0, 1, or 2, and
n''' is 1 or 2.

Further there is included as substituted amino a bicyclic amino group, such as those selected from

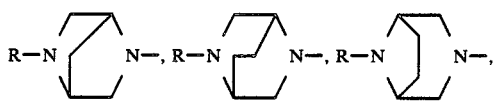

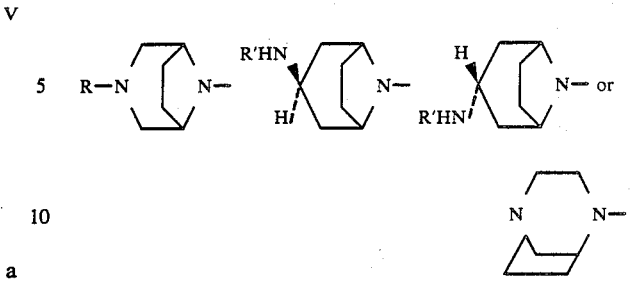

in which R is hydrogen, alkyl of one to three carbon atoms, hydroxyalkyl of two or three carbon atoms, benzyl or p-aminobenzyl, and R' is hydrogen or alkanoyl of one to three carbon atoms.

Preferred amino groups are piperazine or N-methylpiperazine; a pyrrolidine of the formula

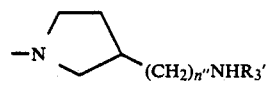

in which n'' is 0 or 1 and R$_3$' is hydrogen, methyl, ethyl, 1- or 2-propyl; a spiroamine of the formula

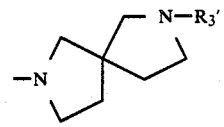

in which R$_3$' is as defined above, or the above bridged amino groups in which R and R' are also defined above.

Particularly preferred 7-substituted amino-1-cyclopropyl-6,8-difluoro-1,4-dihydro-4-oxo-3-quinolinecarboxylic acids prepared by the improved process of the present invention are the following:

7-[3-(aminomethyl)-1-pyrrolidinyl]-1-cyclopropyl-6,8-difluoro-1,4-dihydro-4-oxo-3-quinolinecarboxylic acid;

1-cyclopropyl-7-[3-[(ethylamino)methyl]-1-pyrrolidinyl]-6,8-difluoro-1,4-dihydro-4-oxo-3-quinolinecarboxylic acid;

1-ethyl-7-[3-[(ethylamino)methyl]-1-pyrrolidinyl]-6,8-difluoro-1,4-dihydro-4-oxo-3-quinolinecarboxylic acid;

7-[3-amino-1-pyrrolidinyl]-1-cyclopropyl-6,8-difluoro-1,4-dihydro-4-oxo-3-quinolinecarboxylic acid;

1-cyclopropyl-6,8-difluoro-1,4-dihydro-7-[3-[(methylamino)methyl]-1-pyrrolidinyl]-4-oxo-3-quinolinecarboxylic acid;

1-cyclopropyl-7-[3-(ethylamino)-1-pyrrolidinyl]-6,8-difluoro-1,4-dihydro-4-oxo-3-quinolinecarboxylic acid;

1-cyclopropyl-6,8-difluoro-1,4-dihydro-7-[3-[[(1-methylethyl)amino ]methyl]-1-pyrrolidinyl]-4-oxo-3-quinolinecarboxylic acid;

7-(2,5-diazabicyclo[2.2.2]oct-2-yl)-1-cyclopropyl-6,8-difluoro-1,4-dihydro-4-oxo-3-quinolinecarboxylic acid;

7-[3-(exo-amino)-8-azabicyclo[3.2.1]oct-8-yl]-1-cyclopropyl-6,8-difluoro-1,4-dihydro-4-oxo-3-quinolinecarboxylic acid;

7-(1,4-diazabicyclo[3.2.1]oct-4-yl)-1-cyclopropyl-6,8-difluoro-1,4-dihydro-4-oxo-3-quinolinecarboxylic acid;

1-cyclopropyl-6,8-difluoro-1,4-dihydro-7-(5-methyl-2,5-diazabicyclo[2.2.1]hept-2-yl)-4-oxo-3-quinolinecarboxylic acid;

1-cyclopropyl-7-[2,5-diazabicyclo(2.2.1)hept-2-yl]-6,8-difluoro-1,4-dihydro-4-oxo-3-quinolinecarboxylic acid, and the pharmaceutically acceptable acid addition or base salts thereof.

As previously described, the compounds of Formula I are useful as antibacterial agents against both gram-positive and gram-negative bacteria.

The process of the present invention in its first aspect is a new and improved economical method for preparing antibacterial agents of Formula I. The steps, reagents, and conditions, involved lend the overall process commercially feasible. No special reactors or extreme temperatures requiring expenditure of energy are required. For example, 1-alkyl or 1-cycloalkyl-6,7,8-trifluoro-4-oxo-quinoline-3-carbonitrile of Formula III is prepared from tetrafluorobenzoyl chloride using a simple two-pot procedure. Reaction of the acid chloride with tert.butyl cyanoacetate using at least two equivalents of base, e.g., sodium hydride, potassium tert.-butoxide, and the like, followed by acid work-up gives the cyano keto ester of Formula II. Treatment of this compound with triethylorthoformate or trimethylorthoformate and acetic anhydride at reflux gives an intermediate of the Formula VI

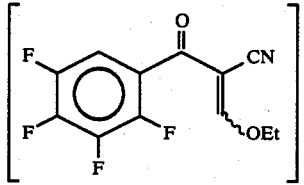
VI which is not isolated but treated in situ with 0.8 to 1.2 equivalents of an amine of the formula $R_2NH_2$ at ambient temperature, e.g., 20°–30° C., to afford another intermediate of the formula:

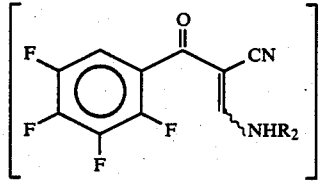
VII which also is not isolated but heated in situ at reflux in a polar aprotic solvent such as, for example, dimethylsulfoxide, N,N-dimethylformamide, N-methylpyrrolidone, dimethylacetamide, sulfolane, acetonitrile, and hexamethylphosphoramide (HMPTA), preferably dimethylsulfoxide, in the presence of at least one equivalent of a tertiary amine, such as, for example, triethylamine, tripropylamine, N,N-diisopropylethylamine, N,N-dimethylaniline, 4-(dimethylamino)pyridine, $N,N,N^1,N^1$-tetramethylethylenediamine tributylamine, N-methylpiperidine, 1,8-diazabicyclo [5.4.0]-undec-7-ene, preferably triethylamine.

The cyanoquinoline of Formula III is then reacted with at least one equivalent of the appropriate amine defined above as "A" displacing the 7-fluoro atom in the compound of Formula III in the absence, but preferably, the presence of a tertiary amine such as, for example, triethylamine, tripropylamine, N,N-diisopropylethylamine, N,N-dimethylaniline, 4-(dimethylamino)pyridine, $N,N,N^1,N^1$-tetramethylethylenediamine, tributylamine, N-methylpiperidine, 1,8-diazabicyclo[5.4.0]-undec-7-ene, preferably triethylamine. When amine "A" contains an additional amino group, for example on pyrrolidine, said group may, if desired, be protected by a known amino-protecting group, such as benzyloxycarbonyl, alkoxycarbonyl, e.g., ethoxycarbonyl, methoxycarbonyl or preferably tert.-butoxycarbonyl. The resulting protected or unprotected 1-alkyl or 1-cycloalkyl-7-amino-6,8-difluoro-1,4-dihydro-4-oxoquinoline-3-carbonitrile is hydrolyzed in situ to the final product of Formula I by converting the nitrile to the carboxylic acid and removing any protecting group. The hydrolysis is carried out first with concentrated hydrochloric acid at 120°–150°. Alternatively, 98% sulfuric acid treatment followed by aqueous sulfuric acid may be employed to convert the nitrile group to the carboxylic acid group.

The starting material for the present invention is 2,3,4,5-tetrafluorobenzoyl chloride which is easily prepared by known methods from tetrafluorobenzoic acid. Tetrafluorobenzoic acid is in turn prepared by decarboxylation of tetrafluorophthalic acid at 145° C. as described in G. C. Yakobson, et al, in Zhurnal Obshchei Khimii, 36(1), pgs 139–42 (1966) or as described in copending U.S. application Ser. No. 773,490 of Sept. 9, 1985, which involves heating tetrafluorophthalic acid with a base catalyst in a polar, aprotic solvent at a temperature of 90° to 140° C.

Compounds of Formula IV, where R is COOR', may also be prepared from 2,3,4,5-tetrafluorobenzoyl chloride. The acid chloride is first treated with the appropriate half ester of malonic acid at low temperatures and in the presence of base such as n-butyllithium, followed by acid work-up to afford the appropriate keto ester of the formula

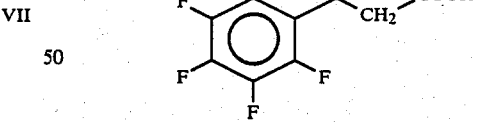
VIII

Compounds of Formula VIII may alternatively be prepared by reacting tetrafluorobenzoyl chloride with a corresponding tert-butyl malonate, e.g., methyl or ethyl, in the presence of sodium hydride or triethylamine magnesium chloride in acetonitrile or tetrahydrofuran to give a compound of the Formula IX

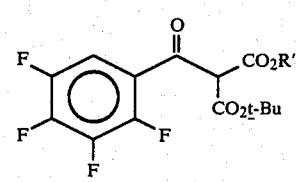
IX

Treatment of this compound with hydrogen chloride or trifluoromethanesulfonic acid in a solvent such as toluene, methylene chloride, tetrahydrofuran, n-butylether, diethylether or a related aprotic solvent affords the desired compound of Formula VIII.

Treatment of a compound of Formula VIII with triethylorthoformate or trimethylorthoformate and acetic anhydride followed by at least one equivalent of an amine of the formula RNH$_2$ at ambient temperature gives the desired intermediate of Formula IV.

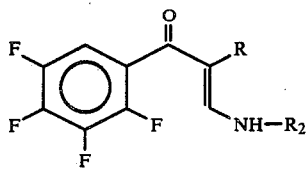

The substituted amines sused herein are either known compounds or they may be prepared from known starting materials by standard procedures or by variations thereof. For example, 3-pyrrolidinemethanamines having the structural Formula D

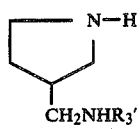

may be readily prepared from the known starting material methyl 5-oxo-1-(phenylmethyl)-3-pyrrolidinecarboxylate, A, [J. Org. Chem., 26, 1519 (1961)] by the following reaction sequence.

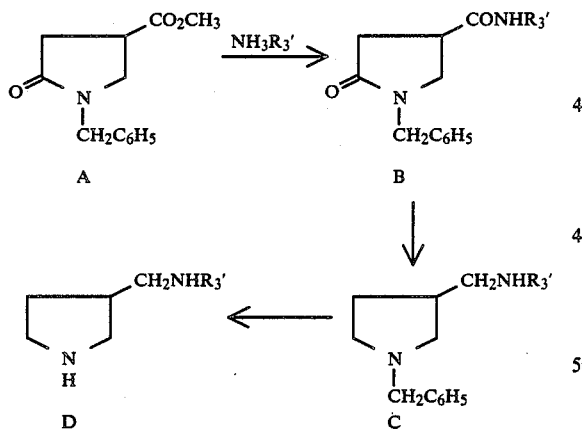

The compound wherein R$_3'$ is hydrogen, namely 3-pyrrolidinemethanamine, has been reported in J. Org. Chem., 26, 4955 (1961).

Thus Compound A may be converted to the corresponding amide B by treatment with R$_3'$NH$_2$; for example, a saturated solution of ethylamine in an alkanol such as methyl alcohol may be utilized. The diamide B may next be reduced to produce the corresponding diamine C. This reduction may be carried out using lithium aluminum hydride, for example, in a convenient solvent such as tetrahydrofuran. Compound C may next be debenzylated, for example using hydrogen and 20% palladium on carbon catalyst to produce the diamine D. Alternatively, when R$_3$=H in C, the primary amine function may be protected by acylation with an acyl halide such as acetyl chloride by well known procedures. The primary amine function of C may also be converted to a carbamate ester such as the ethyl ester by treatment with ethyl chloroformate in the presence of a base such as 1,8-diazabicyclo[5.4.0]undec-7-ene in a convenient solvent such as methylene chloride. The benzyl group may next be removed, for example as described above for Compound C, thereby producing Compound D where R$_3$ is —CO$_2$Et, which after conversion to a compound of the type VIa or VIb may be reacted with a compound having the structural formula IV or V to thereby produce a corresponding compound having the structural formulae I or Ia. The —CO$_2$Et group may be removed by standard procedures.

Likewise spiroamino compounds may be readily prepared from the known starting material 3-ethoxycarbonyl-5-oxo-3-pyrrolidineacetic acid ethyl ester [J. Org. Chem., 46, 2757 (1981)] by the following reaction sequence.

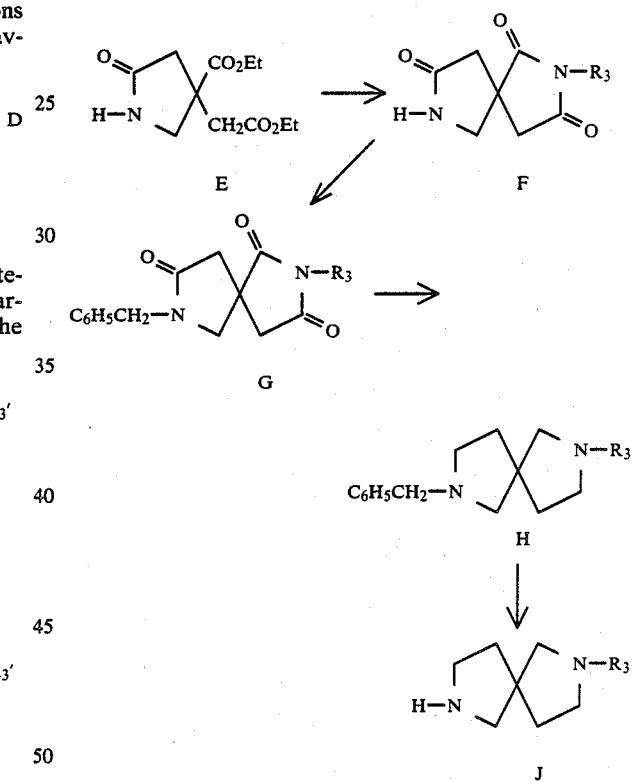

The compound 2,7-diazaspiro[4.4]nonane where R$_3$ is H is described in the above reference. Thus Compound E may be converted to the corresponding amide F by treatment with R$_3$NH$_2$, for example, methyl amine in water followed by benzylation which may be carried out with sodium hydride and benzyl chloride to give G. Reduction to the diamine H may be accomplished with lithium aluminum hydride. Subsequent debenzylation, for example, with hydrogen and 20% palladium on carbon catalyst produces the diamine J.

The bridged amino compounds are either known compounds or they may be prepared from known starting materials by standard procedures or by variations thereof. For example, exo and endo 3-amino-8-azabicyclo [3.2.1] octanes having the structural Formula B and the acetyl derivatives E

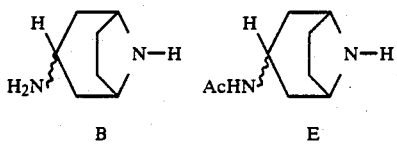

may be readily prepared from the known starting material 8-(phenylmethyl)-8-azabicyclo[3.2.1]octan-3-one oxime, A, [J. Heterocyclic Chem., 19, 485 (1982)] by the following reaction sequence.

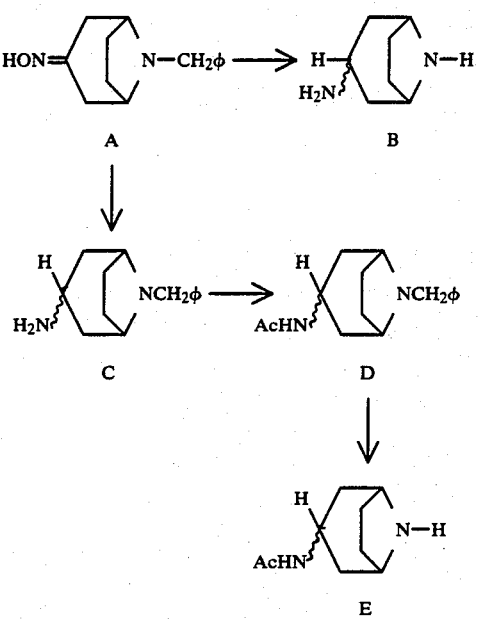

The compounds prepared by the present invention are capable of further forming both pharmaceutically acceptable acid addition and/or base salts. Base salts are formed with metals or amines, such as alkali and alkaline earth metals or organic amines. Examples of metals used as cations are sodium, potassium, magnesium, calcium, and the like. Also included are heavy metal salts such as for example silver, zinc, cobalt, and cerium. such heavy metal salts are effective in the treatment of burns especially when applied to the affected surface of a burn victim either directly or in combination with a physiologically acceptable carrier such as a water dispersible, hydrophilic carrier. Examples of suitable amines are N,N'dibenzylethylenediamine, chloroprocaine, choline, diethanolamine, ethylenediamine, N-methylglucamine, and procaine.

Pharmaceutically acceptable acid addition salts are formed with organic and inorganic acids. Examples of suitable acids for salt formation are hydrochloric, sulfuric, phosphoric, acetic, citric, oxalic, malonic, salicylic, malic, gluconic, fumaric, succinic, ascorbic, maleic, methanesulfonic, and the like. The salts are prepared by contacting the free base form with a sufficient amount of the desired acid to produce either a mono or di, etc salt in the conventional manner. The free base forms may be regenerated by treating the salt form with a base. For example, dilute solutions of aqueous base may be utilized. Dilute aqueous sodium hydroxide, potassium carbonate, ammonia, and sodium bicarbonate solutions are suitable for this purpose. The free base forms differ from their respective salt forms somewhat in certain physical properties such as solubility in polar solvents, but the salts are otherwise equivalent to their respective free base forms for purposes of the invention. Use of excess base where R' is hydrogen gives the corresponding basic salt.

The compounds of the invention can exist in unsolvated as well as solvated forms, including hydrated forms. In general, the solvated forms, including hydrated forms and the like are equivalent to the unsolvated forms for purposes of the invention.

Certain compounds of the invention may exist in optically active forms. The pure D isomer, pure L isomer as well as mixtures thereof, including the racemic mixtures, are contemplated by the invention. Additional assymmetric carbon atoms may be present in a substituent such as an alkyl group. All such isomers as well as mixtures thereof are intended to be included in the invention.

The following nonlimiting examples illustrate the inventor's preferred methods for preparing the compounds of the invention.

EXAMPLE 1 tert-Butyl 2-cyano-3-oxo-3-(2,3,4,5-tetrafluorophenyl)-propionate

A 60% dispersion of sodium hydride in mineral oil (12.8 g) was added to tetrahydrofuran (400 ml) and the mixture cooled with stirring using an ice bath. tert-Butyl cyanoacetate (22.8 g) was added dropwise over a 20 minute period with continued ice bath cooling such that the temperature remained below 10° C. 2,3,4,5-Tetrafluorobenzoyl chloride (34 g) was then added dropwise over a one hour period while maintaining the temperature between −5° C. and 0° C. using an ice-acetone bath. The cooling bath was removed and stirring continued for another 30 minutes while the mixture was warmed to room temperature. The mixture was concentrated to dryness under reduced pressure. Water (1.5 liter) and toluene (100 ml) were added with stirring. The layers were separated and the aqueous layer extracted again with toluene (100 ml). The aqueous layer was acidified to pH 1 using 36% hydrochloric acid. The crystals were collected and washed with excess water and dried under vacuum at room temperature to give tert-butyl 2-cyano-3-oxo-3-(2,3,4,5-tetrafluorophenyl)-propionate (47 g, 93%), mp 90°–92° C.

EXAMPLE 2

1-Cyclopropyl-6,7,8-trifluoro-1,4-dihydro-4-oxoquinoline-3-carbonitrile (Method A)

tert-Butyl 2-cyano-3-oxo-3-(2,3,4,5-tetrafluorophenyl)propionate (3.68 g) was added to a flask containing triethylorthoformate (5.12 g) and acetic anhydride (5.76 g). The resulting solution was heated at reflux for three hours and then concentrated under vacuum to a red oil. During the final stages of distillation the temperature reached 115° C. at 10–15 torr. Dimethylsulfoxide (3.0 g) was added and the resulting solution cooled to 5°–10° C. Cyclopropylamine (0.61 g) in dimethylsulfoxide (3.0 g) was then added with ice bath cooling and continued stirring. The ice bath was removed and the solution maintained overnight at ambient temperature. After 16 hours, triethylamine (3.7 ml) was added and the resulting solution heated at reflux for 1.5 hours. The solution was cooled to 5°–10° C. and the crystals collected, washed with water (3×5 ml) and dried under vacuum at 60° C. to give 1-cyclopropyl-6,7,8-trifluoro-1,4-dihydro-4-oxoquinoline-3-carbonitrile (2.10 g, 69%), mp 213°-215° C.

1-Cyclopropyl-6,7,8-trifluoro-1,4-dihydro-4-oxoquinoline-3-carbonitrile (Method B)

tert-Butyl 2-cyano-3-oxo-3-(2,3,4,5-tetrafluorophenyl)propionate 3.68 g) was dissolved in toluene (10 ml) and acetic acid (0.5 ml) added. The solution was heated at reflux for 70 minutes and then concentrated under vacuum (5-10 torr) to an oil. Triethylorthoformate (5.12 g) and acetic anhydride (5.76 g) were added and the resulting solution heated at reflux for three hours. The solution was concentrated to an oil under vacuum (5-10 torr) and the residual oil cooled to room temperature and dissolved in dimethylsulfoxide (4 ml). The resulting solution was cooled in an ice bath and cyclopropylamine (0.61 g) in dimethylsulfoxide (2 ml) was added with stirring and continued ice bath cooling. After 30 minutes the ice bath was removed and the solution allowed to stand overnight at room temperature. The next day triethylamine (3.7 ml) was added and the resulting solution allowed to reflux for one hour and 45 minutes. The solution was cooled to 5°-10° C. and the crystals collected. The solid was washed with dimethylsulfoxide (1 ml) followed by water (3×10 ml) and then dried under vacuum at 60° C. to give 1-cyclopropyl-6,7,8-trifluoro-1,4-dihydro-4-oxoquinoline-3-carbonitrile (2.21 g, 72%), mp 216°-218° C.

EXAMPLE 3

7-(3-tert-Butyloxycarbonylaminopyrrolidin-1-yl)-1-cyclopropyl-6,8-difluoro-1,4-dihydro-4-oxoquinoline-3-carbonitrile 1-Cyclopropyl-6,7,8-trifluoro-1,4-dihydro-4-oxoquinoline-3-carbonitrile (5.04 g) and 3-(tertbutyloxycarbonylamino)pyrrolidine (3.96 g) were combined in acetonitrile (48 ml). The mixture was heated to reflux at which point all the solids dissolved. After refluxing for 15-20 minutes a precipitate formed. Stirring was continued at reflux overnight (22 hours). Triethylamine (6 ml) was then added and refluxing continued another seven hours before cooling to room temperature. The solid was collected by filtration and then washed with acetonitrile (15 ml) followed by a solution of triethylamine (5 ml) in acetonitrile (5 ml). The solid was dried under vacuum at 50° C. to give 7-[3-(tert-butyloxycarbonylamino)pyrrolidin-1-yl]-1-cyclopropyl-6,8-difluoro-1,4-dihydro-4-oxoquinoline-3-carbonitrile (7.65 g, 93%), mp 249°-250° C. (dec).

EXAMPLE 4

7-(3-Aminopyrrolidin-1-yl)-1-cyclopropyl-6,8-difluoro-1,4-dihydro-4-oxo-quinoline-3-carboxylic acid hydrochloride Hydrochloric acid (36%, 6.5 1) was added to 7-[3-(tert-butyloxycarbonylamino)pyrrolidin-1-yl]-1-cyclopropyl-6,8-difluoro-1,4-dihydro-4-oxoquinoline-3-carbonitrile (1.0 g) and the resulting mixture stirred at room temperature until the solid dissolved and gas evolution ceased (20 minutes). The resulting solution was sealed in a pressure tube and the tube immersed in an oil bath at 135° C. where it was maintained for two hours (p=45 psi). The temperature of the bath was then lowered to 105° C. where it was held for another 16 hours (p=13 psi). The hot solution was filtered through glass wool and tetrahydrofuran (8 ml) was added to the filtrate. This was concentrated at 10-20 torr to a semisolid which was then dissolved in 5% hydrochloric acid (2 ml). Tetrahydrofuran (5 ml) was added and the solution allowed to stand to give crystals which were collected, washed with tetrahydrofuran, and dried under vacuum to give 7-(3-aminopyrrolidin-1-yl)-1-cyclopropyl-6,8-difluoro-1,4-dihydro-4-oxoquinoline-3-carboxylic acid hydrochloride (0.62 g, 69%), mp 308°-311° C. (dec).

The titled compound displays potent antibacterial activity when tested by the microtitration dilution method as described in Heifetz, et al, Antimicrobial Agents and Chemotherapy, 6, 124 (1974). By use of the referenced method, minimum inhibitory concentration values (MICs in $\mu$g/ml) of less than 0.1 were obtained for the following organisms: Enterobacter cloacae MA 2646, Escherichia coli Vogel, Klebsiella pneumoniae MGH-2, Proteus rettgeri M1771, Pseudomones aeruginosa UI-18, Staphyloccus aureus H282, Staphylococcus aureus UC-76, Streptococcus faecalis MGH-2, Streptococcus phenumoiae SV-1, and Streptococcus pyogenes C-203.

EXAMPLE 5

Ethyl 1-Cyclopropyl-6,7,8-trifluoro-1,4-dihydro-4-oxoquinoline-3-carboxylate

A 60% dispersion of sodium hydride in mineral oil (3.1 g) was washed with anhydrous THF (15 ml). The sodium hydride was then treated with fresh anhydrous THF (75 ml) and the mixture cooled with stirring to 0°-5° C. Ethyl tert-butyl malonate (7.3 g) was added dropwise with continued stirring and cooling. After the addition, the temperature of the reaction mixture was lowered to −5° C. and 2,3,4,5-tetrafluorobenzoyl chloride (7.3 g) was added over a 40-minute period while the temperature of the reaction mixture was held below +5° C. The mixture was then concentrated to a semisolid using the rotary evaporator and the residue dissolved in water (240 ml) and toluene (15 ml). The layers were separated and the aqueous layer extracted with toluene (10 ml) and then acidified with 36% hydrochloric acid to pH 3. The oil precipitate was extracted into methylene chloride (3×50 ml). The combined methylene chloride extracts were dried over anhydrous sodium sulfate. The sodium sulfate was washed with methylene chloride and the combined methylene chloride filtrates (total volume 200 ml) were treated with a saturated solution of hydrogen chloride gas in ether (30 ml). The resulting solution was allowed to stand overnight at room temperature and then concentrated using the rotary evaporator to about one third its original volume. This solution was passed through a bed of alumina (Alcoa grade 20, 30-200 mesh, 50 g). The alumina was washed with $CH_2Cl_2$ until the volume of the filtrate reached 300 ml. This was concentrated to give ethyl 2,3,4,5-tetrafluorobenzoylacetate as a white solid (7.4 g, 82%) and 7.0 g of this material was treated directly with triethylorthoformate (5.9 g), acetic anhydride (6.5 g) and the resulting solution allowed to reflux for a period of 3.5 hours. The solution was then subjected to vacuum distillation to remove volatile materials including any unreacted triethylorthoformate. The residual oil was cooled using an ice bath and cyclopropylamine (1.44 g) in dimethylsulfoxide (20 ml) was added with stirring and cooling. The resulting solution was then allowed to stir overnight at room temperature. Triethylamine (8.5 ml) was added and the mixture heated at reflux for three hours. It was then allowed to cool to room temperature and the crystals collected by filtration, washed with water (3×25 ml) and vacuum dried to give ethyl 1-cyclopropyl-6,7,8-trifluoro-1,4-dihydro-4-oxoquinoline-3-carboxylate (6.8 g, 82%): m.p. 169°-171° C.

EXAMPLE 6

Methyl 1-cyclopropyl-6,7,8-trifluoro-1,4-dihydro-4-oxoquinoline-3-carboxylate Magnesium chloride (2.38 g) was added to acetonitrile (25 ml). Methyl tert-butyl malonate (4.4 g) was then added and the mixture cooled with stirring in an ice bath. Triethylamine (7.0 ml) in acetonitrile (5 ml) was added dropwise (5 min) and the resulting thick slurry stirred 15 minutes at 0°-5° C. 2,3,4,5-Tetrafluorobenzoyl chloride (5.31 g) was added dropwise (10 min) followed by more acetonitrile (5 ml). Stirring with cooling at 0°-5° C. was continued for one hour and then overnight at ambient temperature. The mixture was concentrated under reduced pressure (10 torr) using the rotary evaporator and the solid dissolved in toluene (50 ml), n-butyl ether (10 ml) and 6% hydrochloric acid (30 ml) with stirring and cooling. The layers were separated and the organic layer extracted with 6% hydrochloric acid (2×12 ml), dried over sodium sulfate, filtered and the sodium sulfate washed with toluene (10 ml). The combined toluene filtrates were saturated with HCl gas. After standing two days at room temperature, the whole was extracted with water (2×10 ml) and concentrated to a solid which was dried under vacuum to give methyl 2,3,4,5-tetrafluorobenzoyl acetate (5.5 g, 88%). This material was treated with trimethylorthoformate (6.6 g) and acetic anhydride (7.7 g) and the resulting solution heated at reflux for 5.5 hours. The solution was then concentrated under vacuum at 10 torr. In the final stages of the distillation, the temperature reached 95°-100° C. The oily residue was dissolved in dimethylsulfoxide (5 ml) and the solution cooled with an ice bath. Cyclopropylamine (1.28 g) dissolved in dimethylsulfoxide (5.6 ml) was added and the resulting solution allowed to stir overnight at room temperature. Triethylamine (6.7 ml) was added and the resulting solution allowed to reflux for three hours. It was then cooled to 5°-10° C., the mixture filtered, the solid washed with water (3×25 ml) and finally vacuum dried at 50° C. to give methyl 1-cyclopropyl-6,7,8-trifluoro-1,4-dihydro-4-oxoquinoline-3-carboxylate (5.3 g, 83%): m.p. 214°-216° C.

EXAMPLE 7

Ethyl 1-cyclopropyl-6,7,8-trifluoro-1,4-dihydro-4-oxoquinoline-3-carboxylate Ethyl 2,3,4,5-tetrafluorobenzoylacetate (15.25 Kg) was charged to a 30 gallon stainless steel still and triethylorthoformate (12.68 Kg) and acetic anhydride (14.3 Kg) were added. The solution was stirred and heated until a gentle reflux was achieved. Heating at reflux was continued for a period of four hours. The solution was then cooled to 75° C. and subjected to vacuum distillation while the temperature was raised again to 110° C. in order to remove all volatiles including unreacted triethylorthoformate. The vacuum was released and the tank purged for several minutes with nitrogen. The residual oil was cooled to 25°-30° C. and then dissolved in dimethylsulfoxide (47 Kg). While maintaining the temperature between 20° and 25° C., cyclopropylamine (3.28 Kg) was added and the resulting solution stirred overnight (16 hours) at 20°-25° C. Triethylamine (14.5 Kg) was added and the solution brought to reflux where it was maintained for three hours. The solution was then allowed to cool over a 2-3 hour period to 24° C. The crystals were collected by centrifugation and washed with demineralized water (120 L) using a spray head. The product was dried under vacuum at 41°-43° C. for 22 hours to give ethyl 1-cyclopropyl-6,7,8-trifluoro-1,4-dihydro-4-oxoquinoline-3-carboxylate (15.1 Kg, 84%): m.p. 169°-171° C.

We claim:

1. A process for the preparation of a compound of the formula

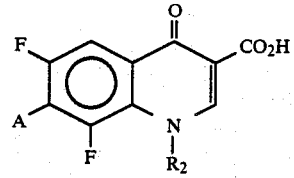

and pharmaceutically acceptable acid addition or base salts thereof, wherein A is a mono- or dialkylamino group of one to four carbon atoms, straight or branched, which alkyl portion may be optionally substituted by hydroxy, amino, methylamino or dimethylamino; a five- to six-membered heterocyclic amino group, which ring may be interrupted by another heteroatom such as oxygen, sulfur, —SO—, —$SO_2$ or N—$R_3$, and which ring may be substituted by alkyl of one to three carbon atoms, hydroxy, alkoxy of one to three carbon atoms, amino, methylamino, ethylamino, aminomethyl, aminoethyl, alkylaminoethyl, or alkylaminomethyl, in which alkyl is one to three carbon atoms, and wherein $R_3$ is hydrogen, alkyl or one to four carbon atoms or cycloalkyl having three to six carbon atoms; a group of the formula

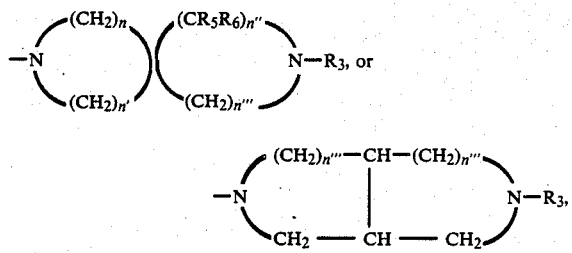

wherein
$R_3$ is as defined above, and
n is 1, 2, 3, or 4;
n' is 1, 2, 3, or 4 wherein n+n' is a total of 2, 3, 4, of 5;
n" is 0, 1, or 2, and
n''' is 1 or 2; or
a bicyclic amino group of the formula

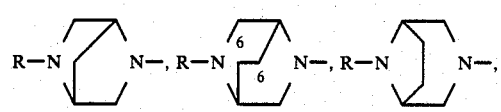

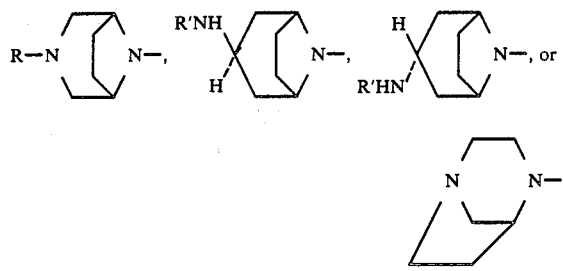

in which R is hydrogen, alkyl of one to three carbon atoms, hydroxyalkyl of two or three carbon atoms, benzyl or p-aminobenzyl, and R' is hydrogen or alkanoyl of one to three carbon atoms, and R₂ is alkyl of one to three carbon atoms or cycloalkyl of three to six carbon atoms, which comprises the steps of (a) reacting 2,3,4,5-tetrafluorobenzoyl chloride with tert-butyl cyanoacetate in the presence of at least two equivalents of sodium hydride or potassium tert.butoxide to give after acid work-up a compound of the formula

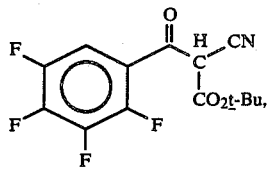

II (b) treating the compound of Formula II with triethylorthoformate or trimethylorthoformate and acetic anhydride at reflux, followed by 0.8 to 1.2 equivalents of an amine of the formula R₂NH₂, wherein R₂ is defined above, at ambient temperature, and followed by heating at reflux in a polar aprotic solvent and in the presence of at least one equivalent of a tertiary amine base to afford a compound of the formula in a two-pot procedure (starting from step (2))

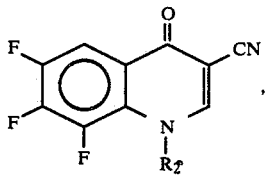

III and (c) reacting said compound of Formula III with at least one equivalent of A wherein A is as defined above followed by acid hydrolysis with hydrochloric acid, or 98% sulfuric acid, followed by aqueous sulfuric acid to give a hydrochloride, sulfate, or hemisulfate salt of a compound of Formula I, and, if desired, converting by known method said salt to the compound of Formula I or a pharmaceutically acceptable acid addition or base salt thereof.

2. A process according to claim 1, wherein the tertiary amine used in step (b) is triethylamine.

3. A process according claim 1, wherein the polar aprotic solvent is dimethylsulfoxide.

4. A process according to claim 1, wherein the acid hydrolysis of step (c) is carried out by heating with concentrated hydrochloric acid at 120°–150° C.

5. A process according to claim 1, wherein A is a five- or six-membered heterocyclic amino group, which may be interrupted by N—R₃, in which ring may be substituted by alkyl of one to three carbon atoms, amino, methylamino, ethylamino, alkylaminoethyl, or alkylaminoethyl in which alkyl has one to three carbon atoms, and wherein R₃ is hydrogen or alkyl of one to four carbon atoms.

6. A process according to claim 1, wherein A is piperazine, N-methylpiperazine or a pyrrolidine of the formula

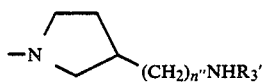

in which n" is 0 or 1 and R₃' is hydrogen, methyl, ethyl, 1- or 2-propyl.

7. A process according to claim 1, wherein A is of the formula

in which R₃' is hydrogen, methyl, ethyl, 1- or 2-propyl.

8. A process according to claim 1, wherein A is of the formula

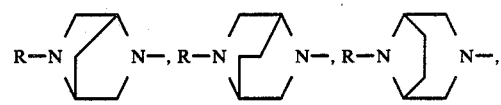

in which R is hydrogen, methyl, ethyl, 1- or 2-propyl, hydroxyethyl, benzyl, or p-aminobenzyl, and R' is hydrogen or acetyl.

9. A process according to claim 1 and for the preparation of 7-[3-(aminomethyl)-1-pyrrolidinyl]1-cyclopropyl-6,8-difluoro-1,4-dihydro-4-oxo-3-quinolinecarboxylic acid.

10. A process according to claim 1 and for the preparation of 1-cyclopropyl-7-[3-[(ethylamino)methyl]-1-pyrrolidinyl]-6,8-difluoro-1,4-dihydro-4-oxo-3-quinolinecarboxylic acid.

11. A process according to claim 1 and for the preparation of 7-[3-amino-1-pyrrolidinyl]-1-cyclopropyl-6,8-difluoro-1,4-dihydro-4-oxo-3-quinolinecarboxylic acid.

12. A process according to claim 1 and for the preparation of 1-cyclopropyl-6,8-difluoro-1,4-dihydro-7-[3-

[(methylamino)methyl]-1-pyrrolidinyl]-4-oxo-3-quinolinecarboxylic acid.

13. A process according to claim 1 and for the preparation of 1-cyclopropyl-7-[3-(ethylamino)-1-pyrrolidinyl]-6,8-difluoro-1,4-dihydro-4-oxo-3-quinolinecarboxylic acid.

14. A process according to claim 1 and for the preparation of 1-cyclopropyl-6,8-difluoro-1,4-dihydro-7-[3-[[(1-methylethyl)amino]methyl]-1-pyrrolidinyl]-4-oxo-3-quinolinecarboxylic acid.

15. A process according to claim 1 and for the preparation of 7-(2,5-diazabicyclo[2.2.2]oct-2-yl)-1-cyclopropyl-6,8-difluoro-1,4-dihydro-4-oxo-3-quinolinecarboxylic acid.

16. A process according to claim 1 and for the preparation of 7-[3-(exo-amino)-8-azabicyclo [3.2.1]oct-8-yl]-1-cyclopropyl-6,8-difluoro-1,4-dihydro-4-oxo-3-quinolinecarboxylic acid.

17. A process according to claim 1 and for the preparation of 7-(1,4-diazabicyclo[3.2.1]oct-4-yl)-1-cyclopropyl-6,8-difluoro-1,4-dihydro-4-oxo-3-quinolinecarboxylic acid.

18. A process according to claim 1 and for the preparation of 1-cyclopropyl-6,8-difluoro-1,4-dihydro-7-(5-methyl-2,5-diazabicyclo[2.2.1]hept-2-yl)-4-oxo-3-quinolinecarboxylic acid.

19. A process according to claim 1 and for the preparation of 1-cyclopropyl-7-(2,5-diazabicyclo[2.2.1]hept-2-yl)-6,8-difluoro-1,4-dihydro-4-oxo-3-quinolinecarboxylic acid.

20. A process according to claim 1 and for the preparation of 1-ethyl-7-[3-[(ethylamino)methyl]-1-pyrrolidinyl]-6,8-difluoro-1,4-dihydro-4-oxo-3-quinolinecarboxylic acid.

* * * * *